US012776033B2

(12) United States Patent
Fujita

(10) Patent No.: US 12,776,033 B2
(45) Date of Patent: Oct. 27, 2026

(54) MEDICAL IMAGING APPARATUS AND CONTROL METHOD OF THE SAME

(71) Applicant: FUJIFILM Healthcare Corporation, Chiba (JP)

(72) Inventor: Mitsuyo Fujita, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 290 days.

(21) Appl. No.: 18/426,291

(22) Filed: Jan. 29, 2024

(65) Prior Publication Data

US 2024/0281963 A1 Aug. 22, 2024

(30) Foreign Application Priority Data

Feb. 20, 2023 (JP) ................................ 2023-024093

(51) Int. Cl.

| | |
|---|---|
| ***G06T 7/00*** | (2017.01) |
| ***A61B 34/20*** | (2016.01) |
| ***G06T 7/60*** | (2017.01) |
| ***G06T 7/73*** | (2017.01) |
| ***G06V 20/50*** | (2022.01) |
| ***G06V 40/10*** | (2022.01) |

(52) U.S. Cl.

CPC ............ *G06T 7/0012* (2013.01); *A61B 34/20* (2016.02); *G06T 7/60* (2013.01); *G06T 7/74* (2017.01); *G06V 20/50* (2022.01); *G06V 40/10* (2022.01); *A61B 2034/2055* (2016.02); *A61B 2034/2065* (2016.02); *G06T 2207/10081* (2013.01); *G06T 2207/30004* (2013.01); *G06T 2207/30196* (2013.01)

(58) Field of Classification Search

CPC ........... G06T 7/0012; G06T 7/60; G06T 7/74; G06T 2207/10081; G06T 2207/30004; G06T 2207/30196; A61B 34/20; A61B 2034/2055; A61B 2034/2065; A61B 6/0487; A61B 6/545; A61B 6/547; A61B 6/589; A61B 6/032; A61B 6/4411; A61B 6/54; G06V 20/50; G06V 40/10

See application file for complete search history.

(56) References Cited

U.S. PATENT DOCUMENTS

2016/0183864 A1* 6/2016 Kusens .................... A61B 5/11
340/573.1
2020/0402272 A1* 12/2020 Xu ............................ G06T 7/73

FOREIGN PATENT DOCUMENTS

JP 2021006993 1/2021

* cited by examiner

*Primary Examiner* — Oneal R Mistry
*Assistant Examiner* — Justin Philip Cascais
(74) *Attorney, Agent, or Firm* — JCIPRNET

(57) ABSTRACT

Provided are a medical imaging apparatus and a control method of the same for specifying a subject from among a plurality of persons included in a camera image.

There is provided a medical imaging apparatus that captures a medical image of a subject placed on a patient table, the medical imaging apparatus including: a camera image acquisition unit that acquires a camera image including the patient table; a person extraction unit that extracts a person from the camera image; and a subject specification unit that specifies the subject from among a plurality of the persons extracted by the person extraction unit, based on a distance between each of the plurality of persons and a reference position set based on the patient table.

11 Claims, 11 Drawing Sheets

MEDICAL IMAGING APPARATUS AND CONTROL METHOD OF THE SAME

CLAIM OF PRIORITY

The present application claims priority from Japanese Patent Application JP 2023-024093 filed on Feb. 20, 2023, the content of which is hereby incorporated by reference into this application.

BACKGROUND OF THE INVENTION

1. Field of the Invention

The present invention relates to a medical imaging apparatus that captures a medical image of a subject, and particularly, to a technique of specifying the subject from among a plurality of persons in a case where the plurality of persons are included in a camera image to be used to set an imaging position.

2. Description of the Related Art

A medical imaging apparatus is an apparatus that detects a signal obtained from an imaging position of a subject, for example, X-rays transmitted through the subject, nuclear magnetic resonance signals generated from the subject, or the like, to capture a medical image to be used to diagnose the subject, or the like. In the medical imaging apparatus, the imaging position is set with respect to the subject on a patient table prior to the capturing of the medical image. It is desirable that the setting of the imaging position be automated.

In JP2021-6993A, it is disclosed that camera images are input into two trained independent deep learning models, and an imaging position is automatically set based on a prediction result obtained from each of the two.

SUMMARY OF THE INVENTION

However, JP2021-6993A lacks consideration for a case where a plurality of persons are included in the camera image. In a case where a plurality of persons are included in the camera image, it is difficult to set the imaging position with respect to the subject because it is unclear which person is the subject.

In that respect, an object of the present invention is to provide a medical imaging apparatus and a control method of the same for specifying a subject from among a plurality of persons included in a camera image.

In order to achieve the above-described object, according to an aspect of the present invention, there is provided a medical imaging apparatus that captures a medical image of a subject placed on a patient table, the medical imaging apparatus comprising: a camera image acquisition unit that acquires a camera image including the patient table; a person extraction unit that extracts a person from the camera image; and a subject specification unit that specifies the subject from among a plurality of the persons extracted by the person extraction unit, based on a distance between each of the plurality of persons and a reference position set based on the patient table.

In addition, according to another aspect of the present invention, there is provided a control method of a medical imaging apparatus that captures a medical image of a subject placed on a patient table, the control method comprising: a camera image acquisition step of acquiring a camera image including the patient table; a person extraction step of extracting a person from the camera image; and a subject specification step of specifying the subject from among a plurality of the persons extracted in the person extraction step, based on a distance between each of the plurality of persons and a reference position set based on the patient table.

According to the present invention, it is possible to provide a medical imaging apparatus and a control method of the same for specifying a subject from among a plurality of persons included in a camera image.

DESCRIPTION OF THE PREFERRED EMBODIMENTS

Hereinafter, examples of a medical imaging apparatus according to the present invention will be described with reference to the accompanying drawings. The medical imaging apparatus is an apparatus that detects a signal obtained from a subject, for example, X-rays transmitted through the subject, nuclear magnetic resonance signals generated from the subject, or the like, to capture a medical image to be used to diagnose the subject, or the like. Hereinafter, as an example of the medical imaging apparatus, an X-ray computed tomography (CT) apparatus that captures a tomographic image of the subject by acquiring X-ray projection images of the subject at various projection angles will be described.

Example 1

Figure 1:
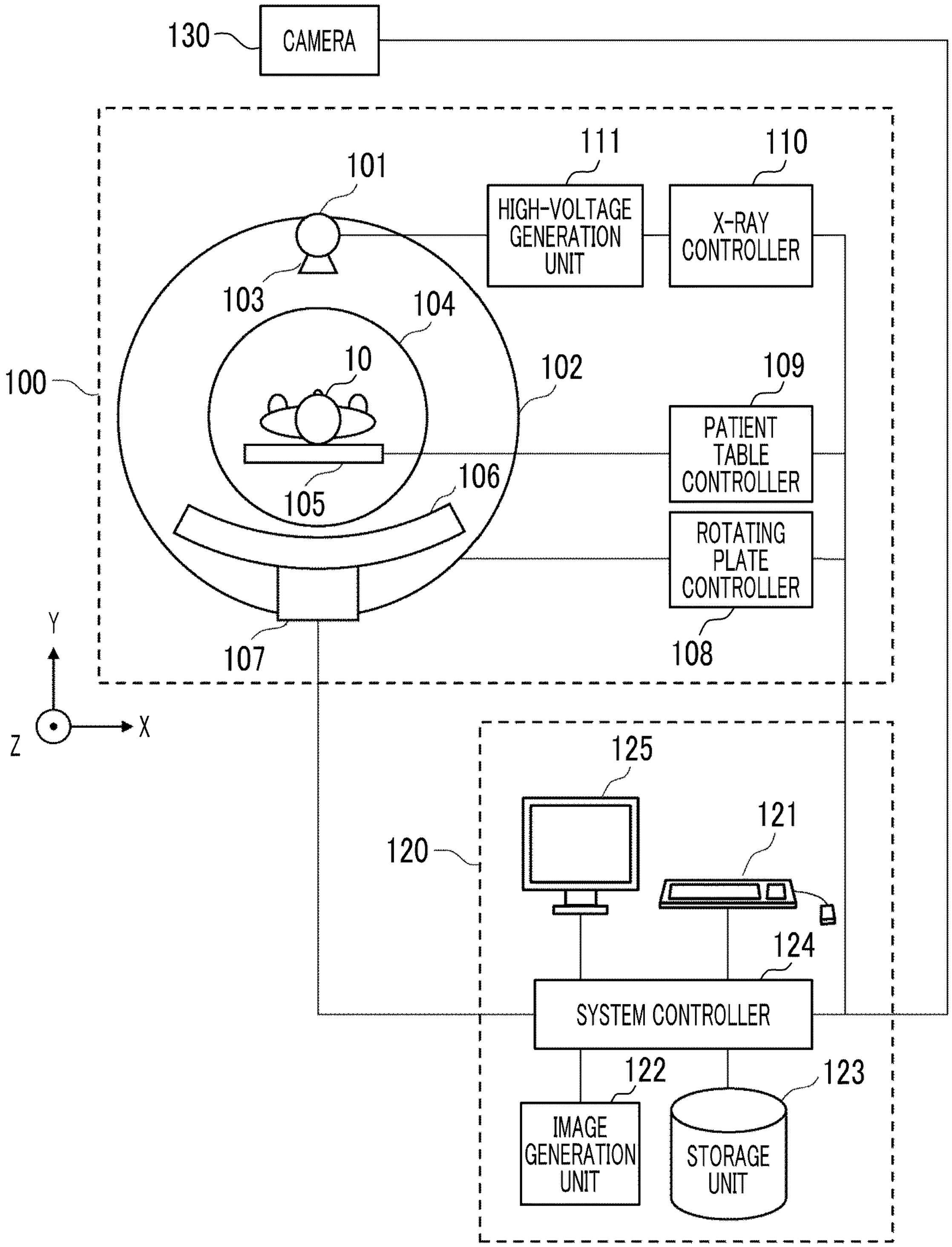
FIG. 1 is a diagram showing an example of an overall configuration of an X-ray CT apparatus of Example 1.

An overall configuration of the X-ray CT apparatus of Example 1 will be described with reference to FIG. 1. The X-ray CT apparatus comprises a scan gantry unit 100, an operation unit 120, and a camera 130. The scan gantry unit 100 and the camera 130 are installed in an imaging room surrounded by a shielding material that blocks X-rays, and the operation unit 120 is installed in an operation room located outside the imaging room.

The scan gantry unit 100 comprises an X-ray source 101, a rotating plate 102, a collimator 103, an X-ray detector 106, a data collection unit 107, a patient table 105, a rotating plate controller 108, a patient table controller 109, an X-ray controller 110, and a high-voltage generation unit 111. The X-ray source 101 is a device that irradiates a subject 10 placed on the patient table 105 with X-rays and is, for example, an X-ray tube device. The collimator 103 is a device that restricts an irradiation range of X-rays. The rotating plate 102 is provided with an opening portion 104 through which the subject 10 placed on the patient table 105 enters, and is also equipped with the X-ray source 101 and the X-ray detector 106 and rotates the X-ray source 101 and the X-ray detector 106 around the subject 10.

The X-ray detector 106 is a device that is disposed to face the X-ray source 101, that comprises a plurality of detection elements which detect X-rays transmitted through the subject 10, and that detects a spatial distribution of X-rays. The detection elements of the X-ray detector 106 are arranged two-dimensionally in a rotation direction and a rotation axis direction of the rotating plate 102. The data collection unit 107 is a device that collects the spatial distribution of X-rays detected by the X-ray detector 106 as digital data.

The rotating plate controller 108 is a device that controls rotation and inclination of the rotating plate 102. The patient table controller 109 is a device that controls up, down, front, back, left, and right movements of the patient table 105. The high-voltage generation unit 111 is a device that generates a high voltage applied to the X-ray source 101. The X-ray controller 110 is a device that controls an output of the high-voltage generation unit 111. The rotating plate controller 108, the patient table controller 109, and the X-ray controller 110 are, for example, a micro-processing unit (MPU) or the like.

The operation unit 120 comprises an input unit 121, an image generation unit 122, a display unit 125, a storage unit 123, and a system controller 124. The input unit 121 is a device that is used to input examination data such as a name of the subject 10, an examination date and time, and an imaging condition, and is, for example, a keyboard, a pointing device, a touch panel, or the like. The image generation unit 122 is a device that generates the tomographic image by using the digital data collected by the data collection unit 107, and is, for example, an MPU, a graphics processing unit (GPU), or the like. The display unit 125 is a device that displays the tomographic image or the like generated by the image generation unit 122, and is, for example, a liquid crystal display, a touch panel, or the like. The storage unit 123 is a device that stores the digital data collected by the data collection unit 107, the tomographic image generated by the image generation unit 122, a program to be executed by the system controller 124, data to be used by the program, and the like, and is, for example, a hard disk drive (HDD), a solid state drive (SSD), or the like. The system controller 124 is a device that controls each unit such as the rotating plate controller 108, the patient table controller 109, and the X-ray controller 110, and is, for example, a central processing unit (CPU).

The camera 130 is a device that images the subject 10 placed on the patient table 105 together with the patient table 105 from above, and is provided on a ceiling of the imaging room or above the scan gantry unit 100 such that the patient table 105 is located at a substantially center of a field of view of the camera 130. A camera image captured by the camera 130 is displayed on the display unit 125, and is used by an operator in the operation room to confirm a state of the subject 10 or is used to set the imaging position with respect to the subject 10. The camera image may be stored in the storage unit 123.

The high-voltage generation unit 111 generates a tube voltage, which is a high voltage applied to the X-ray source 101, based on the imaging condition set via the input unit 121, whereby X-rays corresponding to the imaging condition are emitted to the subject 10 from the X-ray source 101. The X-ray detector 106 detects the X-rays emitted from the X-ray source 101 and transmitted through the subject 10 with a large number of detection elements and acquires the spatial distribution of the transmitted X-rays. The rotating plate 102 is controlled by the rotating plate controller 108 and rotates based on the imaging condition input through the input unit 121, particularly a rotation speed or the like. The patient table 105 is controlled by the patient table controller 109 and moves relative to the rotating plate 102 to move the imaging position set with respect to the subject 10 to an imaging field of view, which is a range in which the transmitted X-rays are detected.

By repeating the irradiation of X-rays by the X-ray source 101 and the detection of X-rays by the X-ray detector 106 with the rotation of the rotating plate 102, projection data, which is the X-ray projection image of the subject 10, is measured at various projection angles. The projection data is associated with a view representing each projection angle, and a channel (ch) number and a column number which are detection element numbers of the X-ray detector 106. The measured projection data is transmitted to the image generation unit 122. The image generation unit 122 generates the tomographic image by performing back-projection processing on a plurality of pieces of projection data. The generated tomographic image is displayed on the display unit 125 or stored in the storage unit 123 as the medical image.

In order to capture the tomographic image, it is necessary to set the imaging position, which is a position at which the tomographic image is captured, with respect to the subject 10. In a case where a plurality of persons are included in the camera image when the camera image is used to set the imaging position, it is not possible to specify which person is the subject 10, which makes it difficult to set the imaging position with respect to the subject 10. In that respect, in Example 1, the subject 10 is specified from among the plurality of persons extracted from the camera image based on distances between the plurality of persons included in the camera image and a reference position set based on the patient table 105, thereby enabling setting of the imaging position using the camera image.

Figure 2:
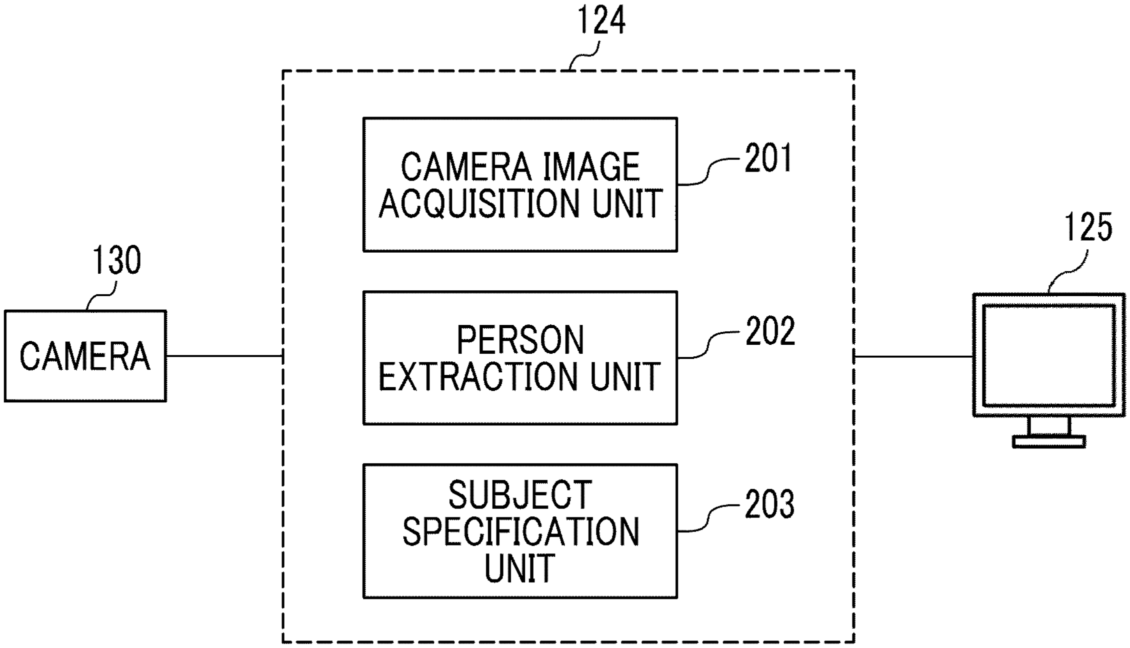
FIG. 2 is a diagram showing an example of functional blocks of Example 1.

The functional blocks of Example I will be described with reference to FIG. 2. It should be noted that these functional blocks may be configured with dedicated hardware using an application specific integrated circuit (ASIC), a field-programmable gate array (FPGA), or the like, or may be configured with software that operates on the system controller 124. In the following description, a case where the functional blocks of Example 1 are configured with software will be described.

In Example 1, a camera image acquisition unit 201, a person extraction unit 202, and a subject specification unit 203 are provided. Hereinafter, each unit will be described.

The camera image acquisition unit 201 acquires the camera image captured by the camera 130. The acquired camera image is a digitized image and is a frame image in a video. The camera image is transmitted from the camera 130 or read out from the storage unit 123.

The person extraction unit 202 extracts a person from the camera image acquired by the camera image acquisition unit 201. The camera image acquisition unit 201 may be configured with, for example, a trained deep learning model. In a case where the camera image includes a plurality of persons, the person extraction unit 202 extracts each of the plurality of persons. In addition, the person extraction unit 202 may detect feature points of each person to be extracted, for example, eyes, nose, ears, shoulders, elbows, wrists, waist, knees, ankles, and the like.

The subject specification unit 203 specifies the subject 10 from among the plurality of persons extracted by the person extraction unit 202. For the specification of the subject 10, the distances between the plurality of persons extracted by the person extraction unit 202 and the reference position set based on the patient table 105 are used. That is, since the subject 10 is placed on the patient table 105, for example, a person having a shortest distance to a center of the patient table 105 is specified as the subject 10.

An example of a flow of processing of Example 1 will be described step by step with reference to FIG. 3.

S301

The camera image acquisition unit 201 acquires the camera image including the patient table 105. The camera image acquired in S301 is a frame image in a video, and may be a camera image transmitted from the camera 130 or a camera image read out from the storage unit 123.

S302

The person extraction unit 202 determines whether or not a person has been extracted from the camera image acquired in S301. The processing returns to S301 via S303 in a case where no person has been extracted from the camera image, and the processing proceeds to S304 in a case where the person has been extracted.

Figure 4:
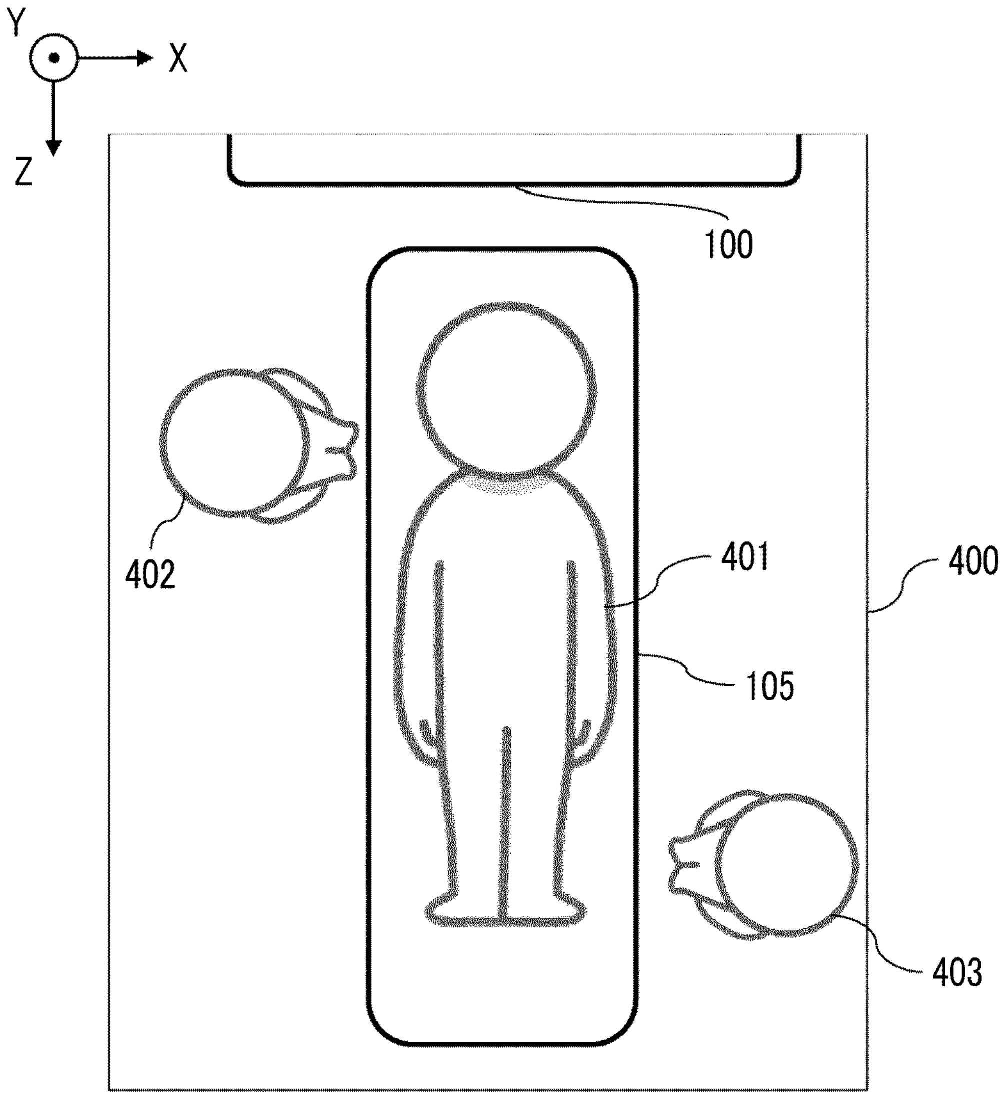
FIG. 4 is a diagram showing an example of a camera image.

FIG. 4 shows an example of a camera image 400 acquired in S301. The camera image 400 illustrated in FIG. 4 includes the scan gantry unit 100 together with the patient table 105 and further includes a first person 401, a second person 402, and a third person 403. The first person 401 is the subject 10 placed on the patient table 105, and the second person 402 and the third person 403 are radiologists who assist the subject 10 or prepare for imaging. Although the person extraction unit 202 can extract a plurality of persons, such as the first person 401, the second person 402, and the third person 403, it is not possible to specify which one of them is the subject 10.

S303

The camera image acquisition unit 201 updates the frame image in the video to the next frame.

S304

The person extraction unit 202 detects the feature points of the person extracted in S302. The detection of the feature points may be based on pose estimation.

Figure 5:
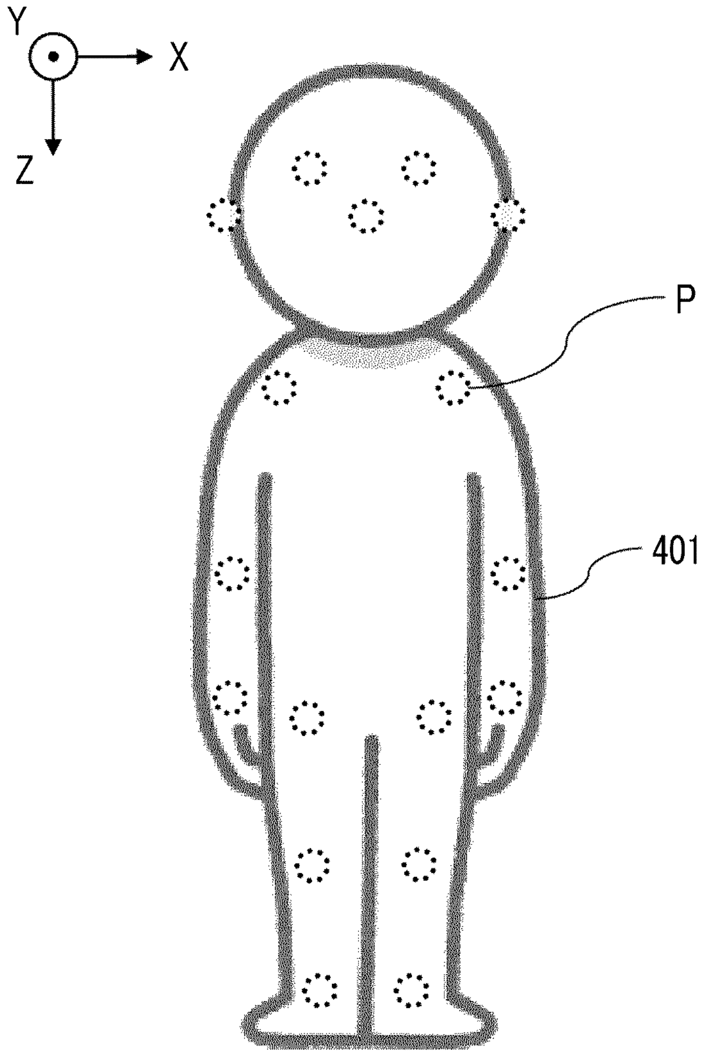
FIG. 5 is a diagram showing an example of feature points of a person.

FIG. 5 shows an example of the detected feature points. In FIG. 5, as feature points P detected from the first person 401 included in the camera image 400 illustrated in FIG. 4, the eyes, nose, ears, shoulders, elbows, wrists, waist, knees, and ankles are indicated by dashed circles. The position of each feature point P is represented by (X,Z) coordinates.

S305

The subject specification unit 203 selects one of the plurality of persons based on the distances between the plurality of persons extracted in S302 and the reference position. In a case where the person extracted in S302 is one person, that person is selected.

Figure 6:
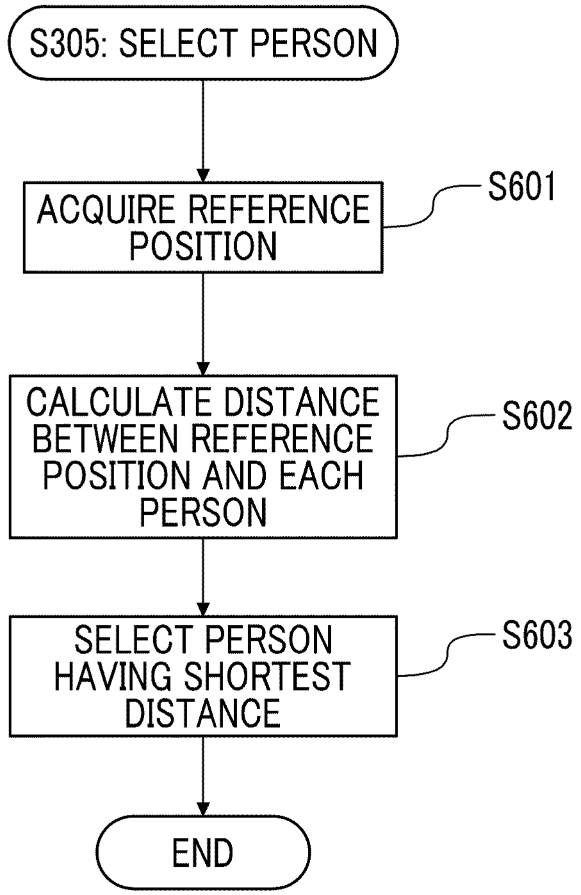
FIG. 6 is a diagram showing an example of a flow of person selection processing.

An example of the flow of the processing of S305 will be described step by step with reference to FIG. 6.

S601

Figure 7:
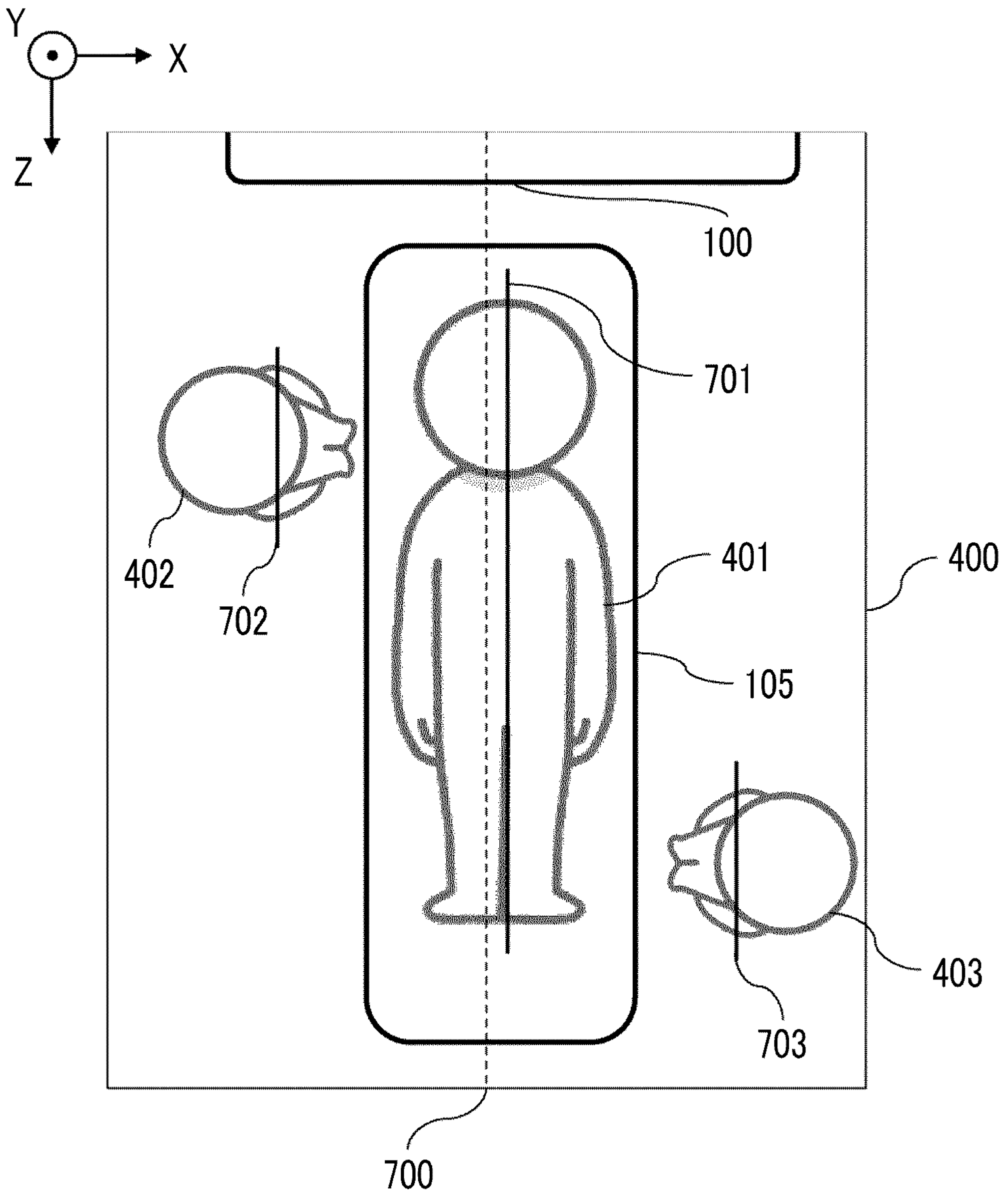
FIG. 7 is a supplementary diagram illustrating the person selection processing.
Figure 8:
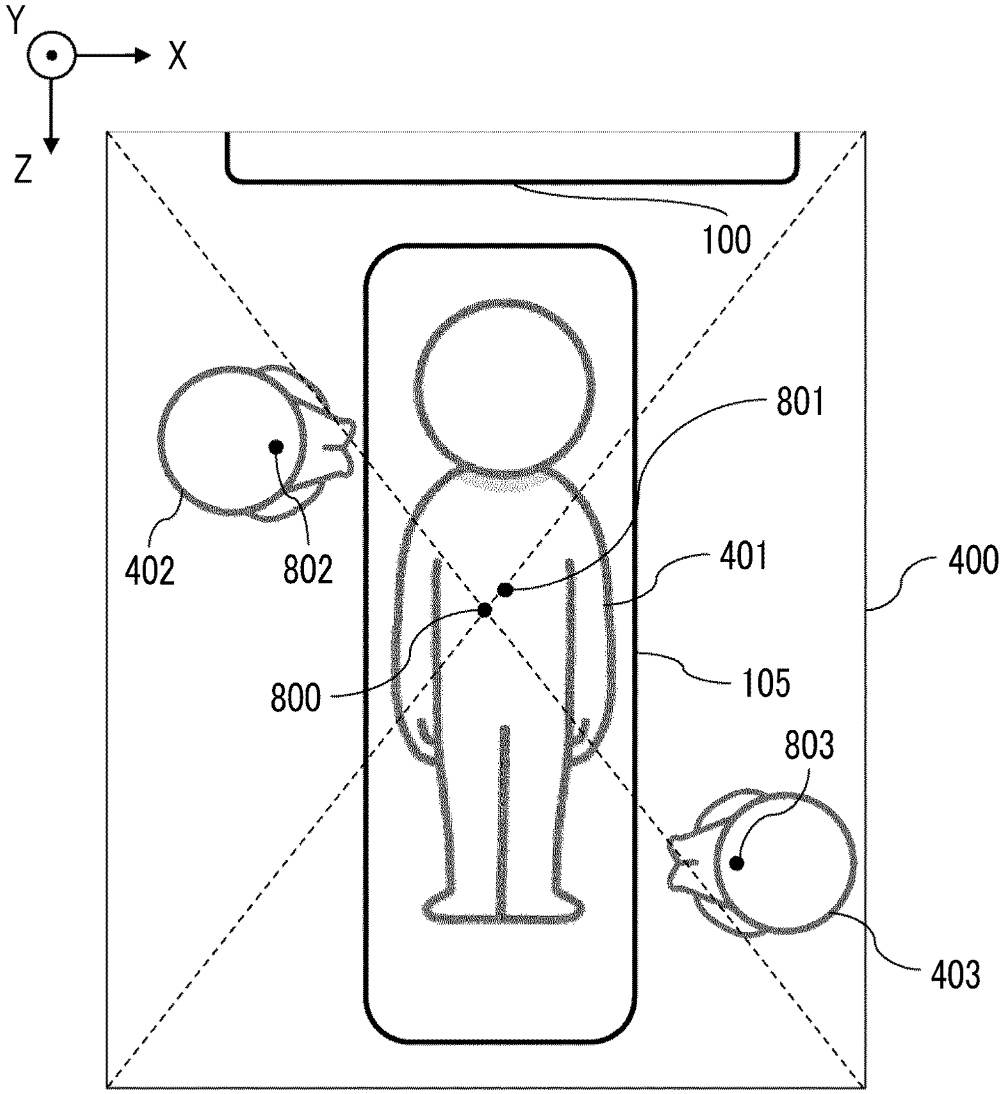
FIG. 8 is a supplementary diagram illustrating the person selection processing.

The subject specification unit 203 acquires the reference position. The reference position is set based on the patient table 105. Since the patient table 105 is located at the substantially center of the camera image, a position of a center line or a center point of the camera image may be set as the reference position. For example, as shown in FIG. 7, in a case where the camera image's center line 700 substantially coincides with a center line of the patient table 105, a position of the camera image's center line 700 may be set as the reference position. As shown in FIG. 8, in a case where the camera image's center point 800 substantially coincides with a center point of the patient table 105, a position of the camera image's center point 800 may be set as the reference position. In a case where the position of the camera image's center line 700 or the camera image's center point 800 is set as the reference position, the reference position is stored in advance in the storage unit 123 and then the reference position need only be read out in S601, so that processing time can be shortened.

Figure 9:
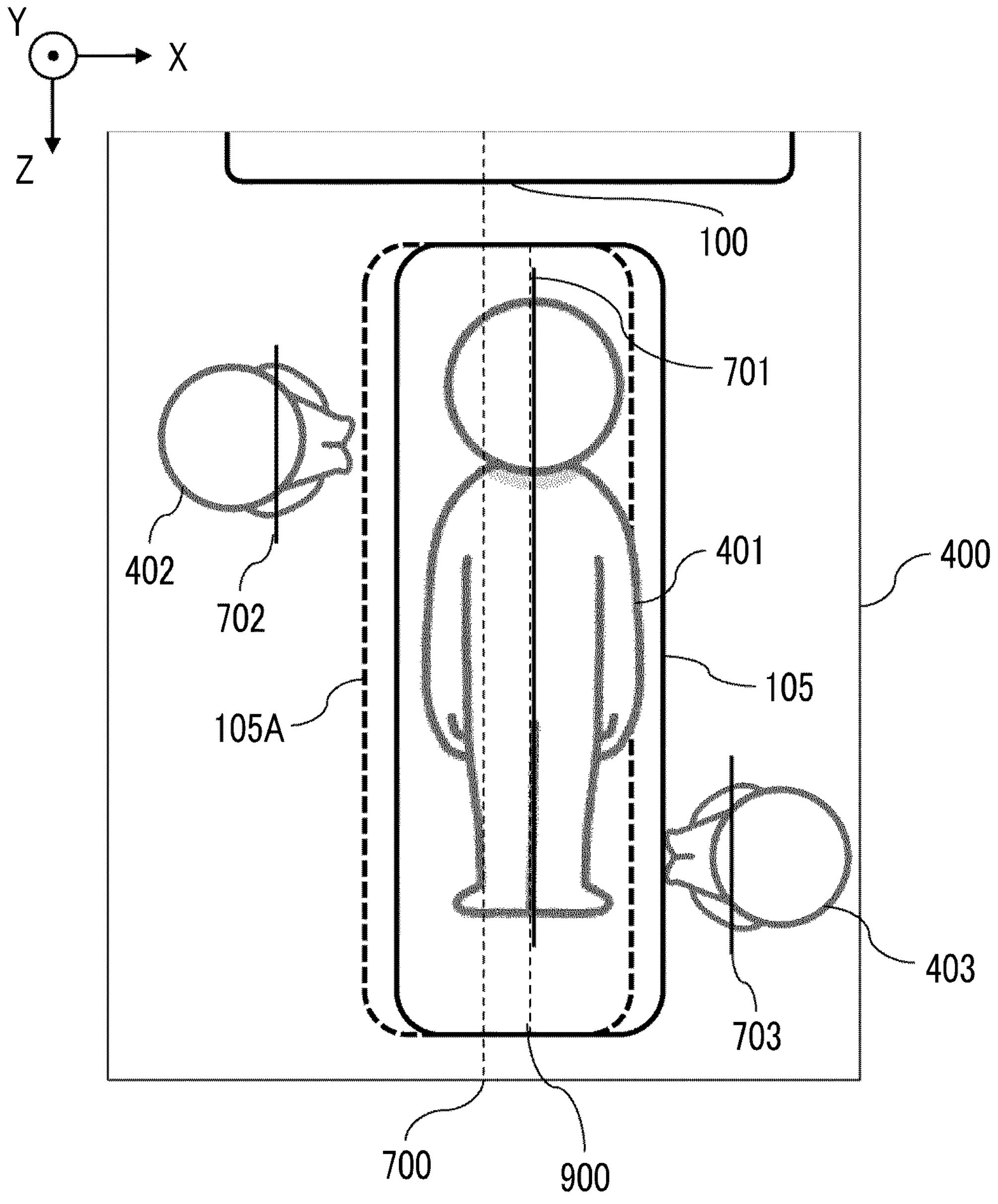
FIG. 9 is a supplementary diagram illustrating the person selection processing.

Further, as shown in FIG. 9, a position of a patient table center line 900, which is the center line of the patient table 105, may be set as the reference position. For example, in a case where the patient table 105 is moved in an X-axis direction in imaging the heart, the patient table center line 900 significantly shifts from the camera image's center line 700. In that respect, the patient table center line 900, which is calculated based on a region of the patient table 105 extracted from the camera image, may be set as the reference position. In a case where the patient table center line 900 is set as the reference position, the subject 10 can be more accurately specified in subsequent processing. In a case where the center point of the patient table 105 is set as the reference position, the subject 10 can also be specified more accurately in subsequent processing.

S602

The subject specification unit 203 calculates a distance between the reference position acquired in S601 and each person extracted in S302.

As shown in FIG. 7, in a case where the position of the camera image's center line 700 is the reference position, the subject specification unit 203 calculates each person's center line by using the plurality of feature points of each person and calculates a distance from the calculated center line of each person to the camera image's center line 700. For example, the distance between the reference position and the first person 401 is a distance from the first person's center line 701, which is calculated using the plurality of feature points of the first person 401, to the camera image's center line 700. Similarly, the distance between the reference position and the second person 402 is a distance from the second person's center line 702 to the camera image's center line 700, and the distance between the reference position and the third person 403 is a distance from the third person's center line 703 to the camera image's center line 700. By calculating the distance from each person's center line to the camera image's center line 700, the distance between the reference position and each person can be calculated with a smaller amount of calculation.

Respective distances between the plurality of feature points of each person and the camera image's center line 700 may be calculated to use an average value of the calculated distances as the distance to the reference position of each person. For example, in a case where the coordinates of three feature points of a certain person are (X1, Z1), (X2, Z2), (X3, Z3) and an X coordinate of the camera image's center line 700 is X0, respective distances from the three feature points to the camera image's center line 700 are X1−X0, X2−X0, and X3−X0. Therefore, the distance of the person to the reference position is (X1+X2+X3−3*X0)/3, which is the average value of the three distances.

Figure 10:
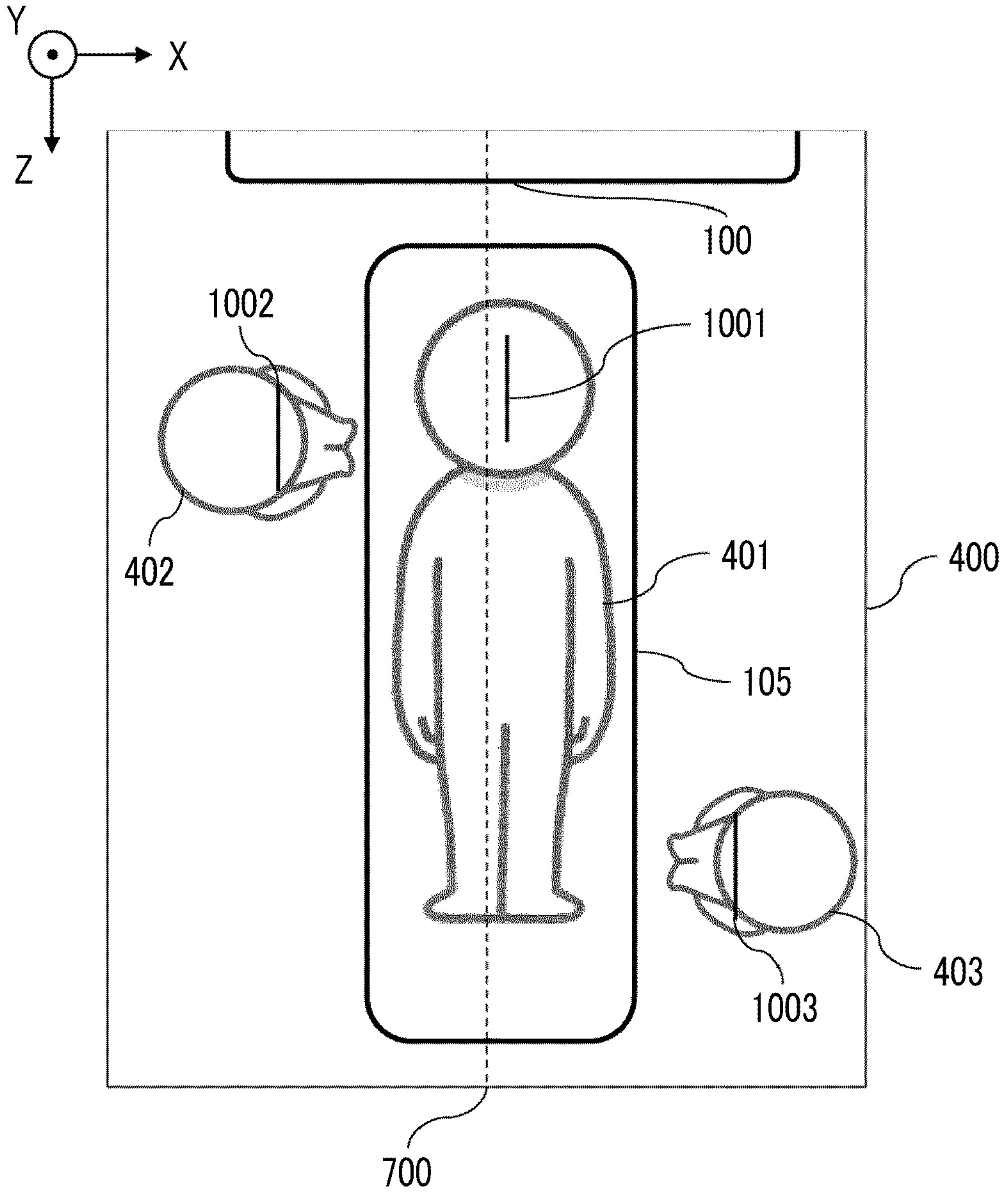
FIG. 10 is a supplementary diagram illustrating the person selection processing.

In addition, each person's center line may be calculated based on a region of interest designated in advance. An examination region may be designated as the region of interest. As shown in FIG. 10, in a case where each person's head part is set as the region of interest, a distance between a head-part center line, which is calculated based on the feature point included in each person's head part, and the camera image's center line 700 is calculated. For example, the distance between the reference position and the first person 401 is a distance from the first person's head-part center line 1001 to the camera image's center line 700. Similarly, the distance between the reference position and the second person 402 is a distance from the second person's head-part center line 1002 to the camera image's center line 700, and the distance between the reference position and the third person 403 is a distance from the third person's head-part center line 1003 to the camera image's center line 700. By calculating each person's center line based on the region of interest designated in advance, the amount of calculation in S602 can be further reduced.

As shown in FIG. 8, in a case where the position of the camera image's center point 800 is the reference position, the subject specification unit 203 calculates a center of gravity of the plurality of feature points of each person as the position of that person, and the distance between the calculated center of gravity and the camera image's center point 800 is used as the distance of that person to the reference position. For example, in a case where the coordinates of three feature points of a certain person are (X1, Z1), (X2, Z2), (X3, Z3), a distance between the center of gravity ((X1+X2+X3)/3, (Z1+Z2+Z3)/3)) of the three feature points and the camera image's center point 800 is the distance of the person to the reference position. By calculating the distance between each person's center of gravity and the camera image's center point 800, the subject 10 can be more accurately specified in subsequent processing even in a case where the radiologist overlaps with the patient table 105 to assist the subject 10.

As shown in FIG. 9, in a case where the position of the patient table center line 900 is the reference position, the subject specification unit 203 calculates the distance from each person's center line to the patient table center line 900. For example, the distance between the reference position and the first person 401 is a distance from the first person's center line 701 to the patient table center line 900. Similarly, the distance between the reference position and the second person 402 is a distance from the second person's center line 702 to the patient table center line 900, and the distance between the reference position and the third person 403 is a distance from the third person's center line 703 to the patient table center line 900.

S603

The subject specification unit 203 selects a person having the shortest distance calculated in S602. By selecting the person having the shortest distance to the reference position, it becomes easier to specify the subject 10 placed on the patient table 105. In any of the examples of FIGS. 7 to 10, the first person 401 having the shortest distance to the reference position among the first person 401, the second person 402, and the third person 403 is selected.

Through the flow of the processing described with reference to FIG. 6, one person is selected from among the plurality of persons based on the distance to the reference position. Return to the description of FIG. 3.

S306

The subject specification unit 203 determines whether or not the person selected in S305 satisfies a condition of the subject 10. The processing returns to S301 via S303 in a case where the person does not satisfy the condition of the subject 10, and the processing proceeds to S307 in a case where the condition is satisfied.

Whether or not the person satisfies the condition of the subject 10 is determined, for example, by whether or not the person is within the region of the patient table 105. That is, determination is made that the condition of the subject 10 is satisfied in a case where the person is within the region of the patient table 105.

In addition, whether or not the condition of the subject 10 is satisfied may be determined based on a motion between frames. That is, while the subject 10 is kept stationary on the patient table 105, the radiologist who assists the subject 10 or prepares for imaging moves around the patient table 105. Therefore, determination is made that the condition of the subject 10 is satisfied in a case where the motion between frames is less than a predetermined threshold value. The motion between frames is calculated based on, for example, a difference value between adjacent frame images in the video.

S307

The subject specification unit 203 specifies the person determined in S306 to satisfy the condition of the subject 10 as the subject 10. The imaging position is set for the person specified as the subject 10 based on, for example, the camera image. In addition, the person specified as the subject 10 may be displayed on the display unit 125. By displaying a specification result on the display unit 125, the operator can confirm whether or not the specified person is appropriate. In a case where the specified person is not appropriate as a result of the confirmation by the operator, the processing may return to S301 via S303.

S308

The camera image acquisition unit 201 determines whether or not the camera image acquired in S301 is a last frame. The processing returns to S301 via S303 in a case where the camera image is not the last frame, and the flow of the processing ends in a case where it is the last frame.

Through the flow of the processing described with reference to FIG. 3, the subject 10 can be specified from among a plurality of persons based on the distance to the reference position set based on the patient table 105 even in a case where the plurality of persons are included in the camera image.

Figure 3:
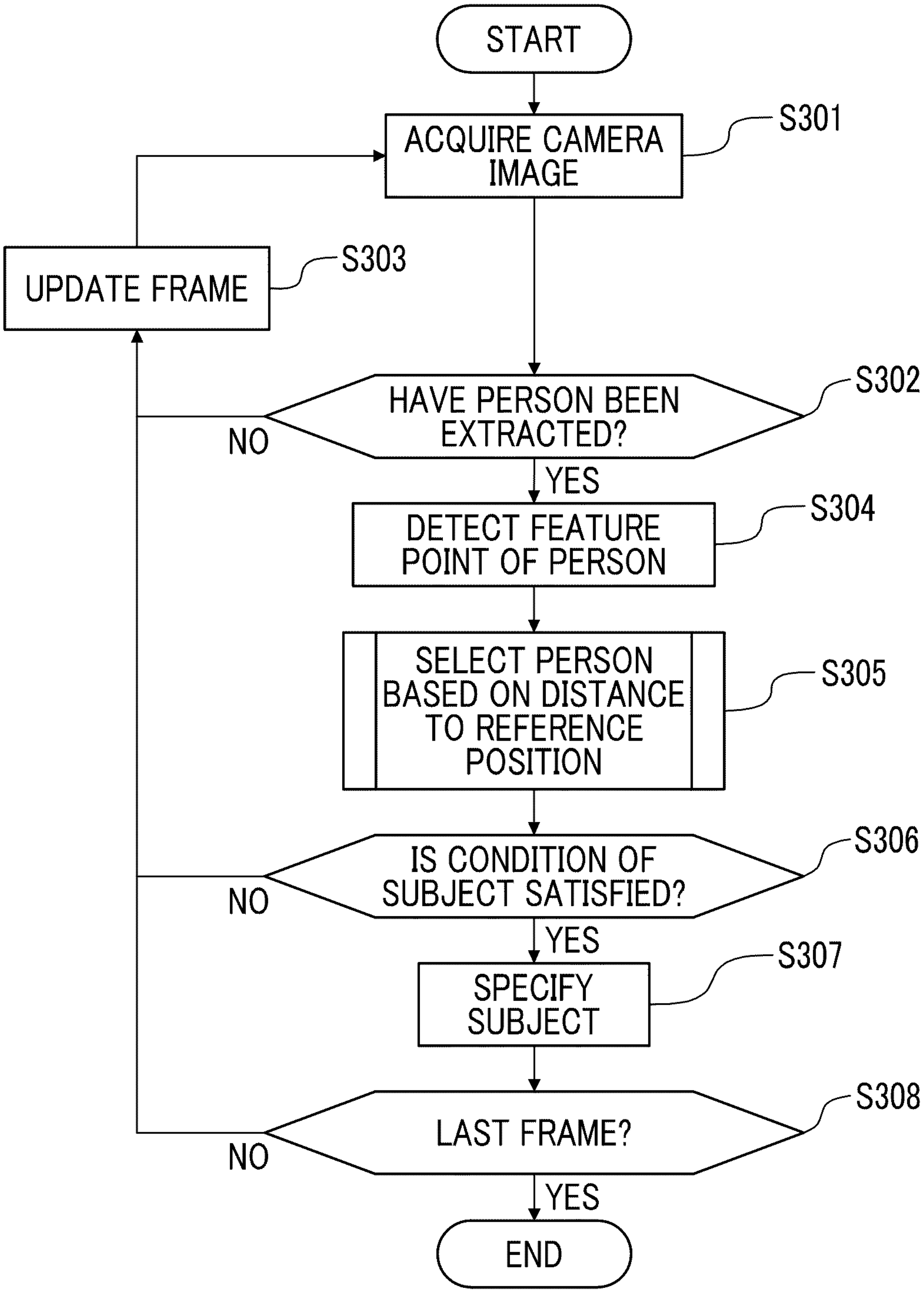
FIG. 3 is a diagram showing an example of a flow of processing of Example 1.
Figure 11:
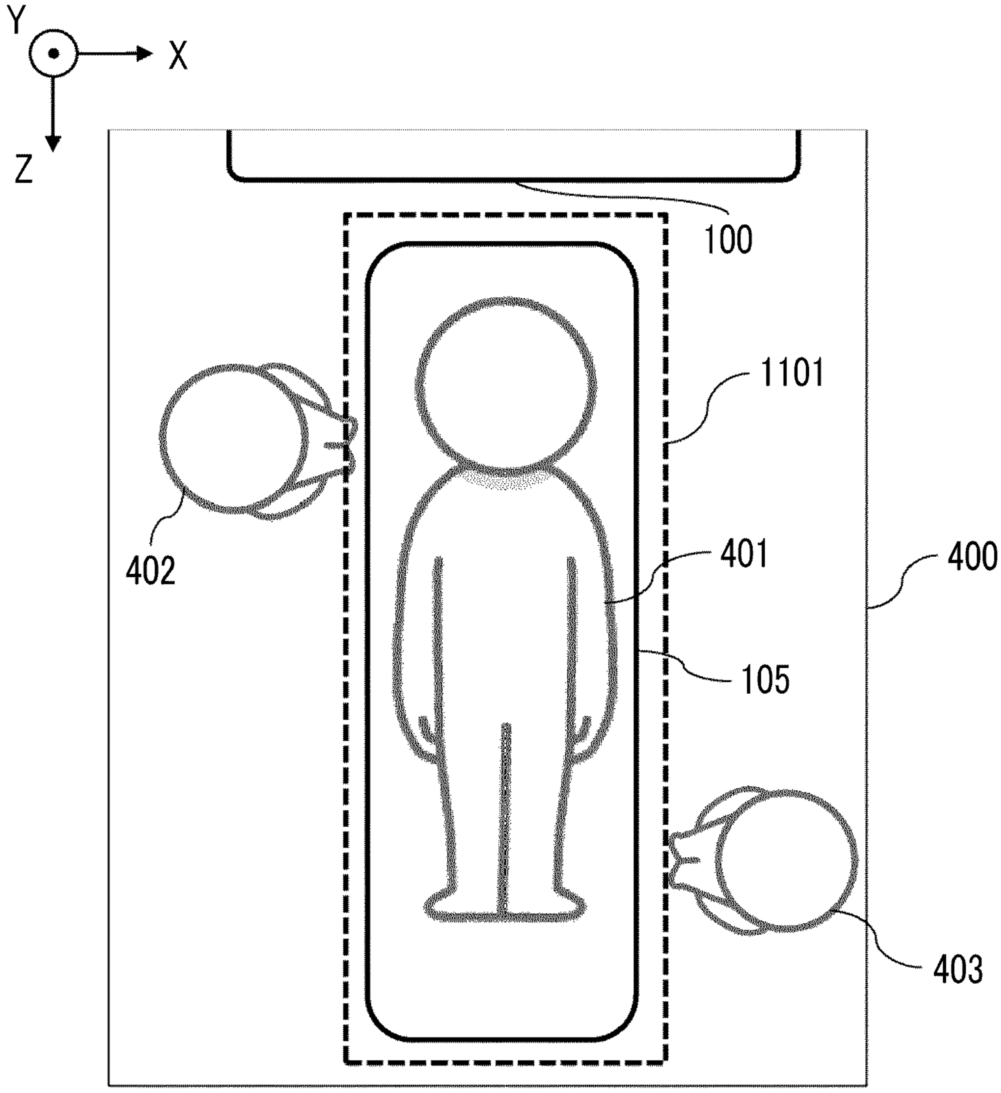
FIG. 11 is a diagram illustrating a person extraction range.

It should be noted that the flow of the processing of Example 1 is not limited to the flow of the processing illustrated in FIG. 3. For example, in a case where a person is extracted from the camera image in S302, a range in which the person is extracted may be limited to a person extraction range 1101 illustrated in FIG. 11. The person extraction range 1101 is a range in which the patient table 105 is movable, and the subject 10 stays within the person extraction range 1101 at the time of preparing for imaging. By limiting the range in which the person extraction unit 202 extracts a person to the person extraction range 1101, the amount of calculation of the person extraction unit 202 can be reduced, and the amount of calculation required for the processing after S304 can also be reduced. Moreover, since the person moving around the patient table 105 is no longer extracted by the person extraction unit 202, the accuracy of the subject specification unit 203 to specify the subject 10 can be improved.

The plurality of embodiments of the present invention have been described above. The present invention is not limited to the above-described embodiments, and the components can be modified and embodied without departing from the gist of the invention. Additionally, a plurality of components disclosed in the above-described embodiments may be combined as appropriate. Furthermore, some components may be deleted from all the components described in the above-described embodiments.

EXPLANATION OF REFERENCES

10: subject
100: scan gantry unit
101: X-ray source
102: rotating plate
103: collimator
104: opening portion
105: patient table
105A: pre-movement patient table
106: X-ray detector
107: data collection unit
108: rotating plate controller
109: patient table controller
110: X-ray controller
111: high-voltage generation unit
120: operation unit
121: input unit
122: image generation unit
123: storage unit
124: system controller
125: display unit
130: camera
201: camera image acquisition unit
202: person extraction unit
203: subject specification unit
400: camera image
401: first person
402: second person
403: third person
700: camera image's center line
701: first person's center line
702: second person's center line
703: third person's center line
800: camera image's center point
801: first person's center point
802: second person's center point
803: third person's center point
900: patient table center line
1001: first person's head-part center line
1002: second person's head-part center line
1003: third person's head-part center line
1101: person extraction range

What is claimed is:

1. A medical imaging apparatus that captures a medical image of a subject placed on a patient table, the medical imaging apparatus comprising:
- a camera image acquisition unit that acquires a camera image including the patient table;
- a person extraction unit that extracts a person from the camera image; and
  - a subject specification unit that specifies the subject from among a plurality of the persons extracted by the person extraction unit, based on a distance between each of the plurality of persons and a reference position set based on the patient table,
- wherein the subject specification unit sets a position of a center line of the camera image as the reference position,
- wherein the person extraction unit detects a plurality of feature points from each of the plurality of persons, and
- the subject specification unit calculates a distance from each person's center line calculated using the plurality of feature points of each person to the center line of the camera image.

2. The medical imaging apparatus according to claim 1, wherein the subject specification unit calculates each person's center line based on a feature point included in a region of interest designated in advance.

3. The medical imaging apparatus according to claim 1, wherein the subject specification unit sets a position of a center point of the camera image as the reference position.

4. The medical imaging apparatus according to claim 1, wherein the subject specification unit extracts a region of the patient table from the camera image and sets a position of a center line or a center point of the extracted region as the reference position.

5. The medical imaging apparatus according to claim 1, wherein the subject specification unit selects a person having a shortest distance from among the plurality of persons.

6. The medical imaging apparatus according to claim 5, wherein the subject specification unit specifies, in a case where the person selected from among the plurality of persons satisfies a predetermined condition, the person as the subject.

7. The medical imaging apparatus according to claim 6, wherein the predetermined condition is that the person is within a region of the patient table.

8. The medical imaging apparatus according to claim 1, wherein the person extraction unit extracts the person from a range in which the patient table is movable.

9. A medical imaging apparatus that captures a medical image of a subject placed on a patient table, the medical imaging apparatus comprising:
- a camera image acquisition unit that acquires a camera image including the patient table;
- a person extraction unit that extracts a person from the camera image; and
- a subject specification unit that specifies the subject from among a plurality of the persons extracted by the person extraction unit, based on a distance between each of the plurality of persons and a reference position set based on the patient table,
  - wherein the subject specification unit sets a position of a center point of the camera image as the reference position,
  - wherein the person extraction unit detects a plurality of feature points from each of the plurality of persons, and
  - the subject specification unit calculates a center of gravity of the plurality of feature points of each person and calculates a distance between the center of gravity and the center point of the camera image.

10. A medical imaging apparatus that captures a medical image of a subject placed on a patient table, the medical imaging apparatus comprising:
- a camera image acquisition unit that acquires a camera image including the patient table;
- a person extraction unit that extracts a person from the camera image; and
- a subject specification unit that specifies the subject from among a plurality of the persons extracted by the person extraction unit, based on a distance between each of the plurality of persons and a reference position set based on the patient table, wherein the subject specification unit selects a person having a shortest distance from among the plurality of persons, wherein the subject specification unit specifies, in a case where the person selected from among the plurality of persons satisfies a predetermined condition, the person as the subject, wherein the predetermined condition is that the person is within a region of the patient table, wherein the predetermined condition is that a motion between frames is less than a threshold value.

11. A control method of a medical imaging apparatus that captures a medical image of a subject placed on a patient table, the control method comprising:

a camera image acquisition step of acquiring a camera image including the patient table;

a person extraction step of extracting a person from the camera image; and a subject specification step of specifying the subject from among a plurality of the persons extracted in the person extraction step, based on a distance between each of the plurality of persons and a reference position set based on the patient table, wherein the subject specification step comprises setting a position of a center line of the camera image as the reference position, wherein the person extraction step comprises detecting a plurality of feature points from each of the plurality of persons, and the subject specification step further comprises calculating a distance from each person's center line calculated using the plurality of feature points of each person to the center line of the camera image.

* * * * *